United States Patent [19]

Su et al.

[11] Patent Number: 4,788,289

[45] Date of Patent: Nov. 29, 1988

[54] PROCESS FOR PREPARING PYRAZINES FROM HYDROXYAMINES

[75] Inventors: Wei-Yang Su; John F. Knifton, both of Austin, Tex.

[73] Assignee: Texaco Inc., White Plains, N.Y.

[21] Appl. No.: 922,918

[22] Filed: Oct. 24, 1986

[51] Int. Cl.$^4$ ............................................. C07D 241/12
[52] U.S. Cl. ..................................... 544/336; 544/358; 544/410
[58] Field of Search ......................... 544/410, 358, 336

[56] References Cited

U.S. PATENT DOCUMENTS

| | | | |
|---|---|---|---|
| 2,813,869 | 11/1957 | Langdon | 544/358 X |
| 3,067,199 | 12/1962 | Langdon | 544/410 |
| 4,097,478 | 6/1978 | Sato | 544/353 |
| 4,233,226 | 11/1980 | Takeda et al. | 549/398 |

FOREIGN PATENT DOCUMENTS

| | | | |
|---|---|---|---|
| 580520 | 7/1959 | Canada | 544/358 |
| 258168 | 12/1985 | Japan | 544/410 |

OTHER PUBLICATIONS

Trost et al, Chem. Abstracts, vol. 93 (1980), entry 71447g.
Tsuji et al, Chem. Abstracts, vol. 102 (1985), entry 185055n.

*Primary Examiner*—Donald G. Daus
*Assistant Examiner*—William A. Teoli, Jr.
*Attorney, Agent, or Firm*—Jack H. Park; Kenneth R. Priem; Cynthia L. Kendrick

[57] ABSTRACT

This invention relates to the cyclocondensation of hydroxyamines to form pyrazines by a process comprising reacting said hydroxyamine in the presence of a catalyst comprising a rhodium, ruthenium or palladium-containing compound and a phosphine-containing compound under mild conditions.

12 Claims, No Drawings

PROCESS FOR PREPARING PYRAZINES FROM HYDROXYAMINES

FIELD OF THE INVENTION

This invention concerns a process for the preparation of pyrazines. More particularly this invention relates to the preparation of pyrazines from a hydroxyamine in the presence of a homogeneous ruthenium, rhodium or palladium-containing compound and a phosphine compound.

BACKGROUND OF THE INVENTION

Previously, the preparation of pyrazine and its derivatives has involved the dehydrogenation of the corresponding piperazines, but the method suffers from the disadvantage that the two classes of chemicals are often difficult to separate.

Pyrazines have also been prepared from diols, for example Japanese Patent No. 79,132,588 discloses the preparation of pyrazines by treating diols with diamines in the gas phase in the presence of compounds such as Zn, Mg, Ce, Mn, Fe, Pd, Pb, P or B. In one example 2,3-butanediol and 1,2-diaminopropane were reacted in the presence of a ZnO catalyst containing $PdSO_4$ at 470°-80° to give a 70% pyrazine product with 100% conversion of the starting materials.

In another Japanese reference, Japanese Patent No. 80,122,769, a method is disclosed for preparing pyrazines from the hydroxydiamine, N-(2-hydroxyethyl)ethylenediamine using a $Cr_2O_3$—CuO catalyst at a temperature from about 265° C. to 300° C. The conversion was about 82% and the yield of pyrazine was about 78%.

Pyrazines have also been prepared from diols plus a diamine through contact in the gas phase in the presence of a zinc-containing catalyst. Such a procedure is disclosed in U.S. Pat. No. 4,097,478.

To our knowledge, the only disclosure of a procedure for making pyrazines from hydroxyamines comes from a recent Japanese Patent Application, No. 60258-168A, which describes subjecting alkanolamines to gaseous reaction conditions in the presence of a zinc-containing catalyst. High temperatures of 300°-500° C. are preferred for this synthesis with this class of catalyst.

The pyrazine products of these syntheses described supra are useful as intermediates for perfumes, pharmaceuticals and agrochemicals. 2,5-Dimethylpyrazine, for example, is useful in cosmetics, flavorings and polymer applications.

It would be a great advantage in the art if pyrazines could be prepared from hydroxyamines under mild reaction conditions. It would also be an advantage if the catalyst system which allowed good conversion and yield also enabled the product to be separated efficiently.

SUMMARY OF THE INVENTION

It has now been discovered that pyrazines can be prepared by cyclocondensation of a hydroxyamine by contacting said hydroxyamine with a catalyst comprising a rhodium, ruthenium or palladium-containing compound and a phosphine-containing compound under mild conditions. The use of a homogeneous catalyst for this synthesis appears to be new.

The pyrazines can be represented by the structural formula:

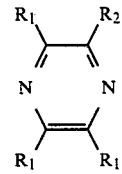

Suitable β- or 1,2-hydroxyamine reactants have the structural formula:

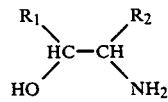

wherein $R_1$ is a hydrocarbon group having one to about 6 carbon atoms, such as an alkyl, alkenyl or cycloalkyl group and $R_2$ is hydrogen or of the class of $R_1$.

DETAILED DESCRIPTION

In the narrower and more preferred practice of this invention, pyrazines are prepared from a hydroxyamine by a process comprising:

(a) Contacting said β-hydroxyamine with a catalyst system comprising a homogeneous transition metal compound selected from the group consisting of ruthenium, rhodium or palladium, plus a phosphine-containing compound, (b) heating said reacting mixture to a temperature at least 100° C. under atmospheric pressure or greater, and (c) separating said pyrazine products contained therein.

The reaction of hydroxyamines to form pyrazines can be represented by the following equation:

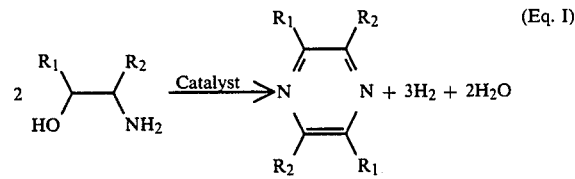

In general, the components of the reaction mixture, including the hydroxyamine, transition metal compound, phosphine compound and optional solvent may be added in any sequence as long as good agitation is employed to provide a good dispersion or homogeneous reaction mixture. For example, the following represent some variations insofar as the addition of catalyst components, solvents and hydroxyamine addition that can be made without departing from the inventive process. These modifications include:

1. The catalyst may be preformed and added to the solvent prior to addition of the hydroxyamine;

2. Preferably, to minimize stability problems with the catalyst, the catalyst is best formed in situ, usually by mixing the solvent and hydroxyamine followed by the addition of the transition metal compound and phosphorous-containing compound to form the reaction mixture.

3. After using either variation 1 or 2 the catalyst-containing reaction mixture is heated until the product is formed.

In order to present the inventive concept in the greatest possible detail to promote its understanding, the following supplementary disclosure is submitted. The basic invention improved upon here is practiced as follows:

The reactant used in the process of this invention comprises a hydroxyamine.

The catalyst comprises a transition metal, phosphine and solvent.

Catalysts which are suitable in the practice of this invention contain transition metals of the group consisting of ruthenium, rhodium or palladium. The transition metal can be chosen from a wide variety of organic or inorganic compounds, complexes, etc. It is only necessary that the catalyst precursor actually employed contain said metal in any of its ionic states. The actual catalytically active species is then believed to comprise ruthenium, rhodium or palladium and phosphine in complex combination with a hydroxyamine in a solvent. The most effective catalyst is believed to be achieved where a ruthenium, rhodium or palladium salt of a mineral acid is mixed with a phosphine compound in a solvent under reaction conditions.

The ruthenium catalyst precursors may take many different forms. For instance, the ruthenium may be added to the reaction mixture in an oxide form, as in the case of, for example, ruthenium(IV) oxide hydrate. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, such as, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

The rhodium-catalyst precursors may also take many different forms. For instance, the rhodium may be added to the reaction mixture in an oxide form, as in the case of, for example, rhodium(III) oxide. Alternatively, it may be added as the salt of a mineral acid, as in the case of rhodium(III) chloride, rhodium bromide and rhodium(III) nitrate, or as the salt of a suitable organic carboxylic acid, such as, for example, rhodium(II) acetate dimer, as well as rhodium complexes with carbonyl-containing ligands, such as rhodium(III) acetylacetonate. The rhodium may also be added to the reaction zone as a carbonyl or hydrido carbonyl derivative. Here, suitable examples include tetrarhodium dodecacarbonyl and hexarhodium hexadecacarbonyl.

The palladium catalyst precursor may take several different forms. For instance, the palladium may be added as the salt of a mineral acid, as in the case of palladium(II) chloride and palladium(II) bromide, or as the salt of a suitable organic carboxylic acid, such as, for example, palladium(II) acetate, as well as palladium complexes with carbonyl-containing ligands such as palladium(II) acetylacetonate. The palladium may also be added to the reaction zone as a carbonyl or carbonyl derivative, or as a nitrile complex, as in the case of dichloro(benzonitrile)palladium(II).

The catalyst compounds are preferably employed with a tertiary phosphine. Suitable tertiary phosphine components used in the preferred catalyst formulation may contain one or more trivalent phosphorous atoms per molecule, wherein the phosphorus is bonded to alkyl, aryl, alkaryl and aralkyl reactants or mixtures thereof. Specific examples of such tertiary phosphines include tri-n-butylphosphine, tri-sec-butylphosphine, trimethylphosphine, triethylphosphine, tri-c-hexylphosphine, triphenylphosphine, tri-p-tolylphosphine, benzyldiphenylphosphine, 1,2-bis(diphenylphosphino)ethane, tri-p-methoxyphenylphosphine, 1,3-bis(diphenylphosphino)propane among others.

In the preferred embodiment of this invention the catalyst comprises a phosphine compound used in conjunction with the rhodium, ruthenium or palladium. The preferred catalyst includes a transition metal salt of a mineral acid and a trialkylphosphine. These components may be added as a preformed complex or complexes, or they may be added separately to the reaction zone. The preferred combinations include: ruthenium-(III) chloride plus tri-n-butylphosphine, $RhCl_3$—$Ph_2P(CH_2)_2PPh_2$, $RuCl_3$—$Ph_2P(CH_2)_3PPh_2$, dichlorotris(triphenylphosphine)ruthenium(II), dichlorodicarbonylbis(triphenylphosphine)ruthenium(II) and hydrido(acetato)tris(triphenylphosphine)ruthenium(II). Preferred rhodium-phosphine combinations include $RhCl_3$—$Ph_2P(CH_2)_3PPh_2$, hydridocarbonyltris(triphenylphosphine)rhodium(I), chlorotris(triphenylphosphine)rhodium(I), chlorocarbonylbis(triphenylphosphine)rhodium(I), and $RhCl_3$—$PBu_3$. Preferred palladium-phosphine combinations include dichlorobis(triphenylphosphine)palladium(II) and tetrakis(triphenylphosphine)palladium(O).

As mentioned above the preferred reactants are hydroxyamines. The hydroxyamines which will work in the process can be represented by the following structural formula:

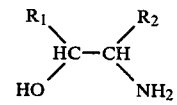

wherein $R_1$ is a hydrocarbon group having one to about 6 carbon atoms, such as an alkyl, alkenyl or cycloalkenyl group and $R_2$ is hydrogen or of the class of $R_1$.

Examples of suitable β-hydroxyamines include, but are not limited, to ethanolamine, 1-amino-2-propanol, 1-amino-2-butanol, 1-amino-2-hexanol and 2-amino-3-butanol. Good results were obtained using 1-amino-2-propanol.

The novel reaction is run most conveniently in the presence of a solvent. The solvent useful in the process of this invention is an oxygenated hydrocarbon, i.e., a compound composed only of carbon, hyrogen and oxygen and one in which the only oxygen atoms present are in ether groups. Generally the oxygenated hydrocarbon will contain 3 to 14 carbon atoms and preferably a maximum of 7 oxygen atoms. The solvent must be substantially inert under reaction conditions.

Ethers which may be utilized as solvents include cyclic, acyclic and heterocyclic ethers, as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, tetraethylene glycol dimethyl ether (tetraglyme) etc.

The preferred solvent in the reaction to produce pyrazines is p-dioxane.

The quantity of transition metal compound, phosphine compound and solvent employed in the instant invention is not critical and may vary over a wide range. In general, the novel process is desirably conducted in the presence of a catalytically effective quantity of active transition metal species, phosphine compound and solvent which gives the desired product in reasonable yield. The reaction proceeds when employing as little as about $1 \times 10^{-6}$ weight percent and even lesser amounts of transition metal.

The upper concentration is dictated by a variety of factors including catalyst cost, partial pressure of carbon monoxide and hydrogen, operating temperature, etc. A transition metal concentration of from about 0.0001 to about 10 weight percent in conjunction with a phosphine concentration of from about 0.001 to about 10 weight percent and a solvent concentration of from zero to about 70% based on the total weight of the reaction mixture, is desirable in the practice of this invention.

The temperature range which can usefully be employed in these syntheses is a variable dependent upon other experimental factors, including the pressure, the concentration and the choice of the particular species of transition metal catalyst, among other things. The range of operability is from about 50° to 300° C. A narrow range of 150°–250° C. represents the preferred temperature range.

Pressures of atmospheric or greater lead to substantial yields of pyrazine products by the process of this invention. A preferred operating range is above 50 psi. The most preferred range is from 100–400 psi, but pressures greater than 400 psi can be used.

The novel process of this invention can be conducted in a batch, semi-continuous or continuous fashion and said material may be recovered by methods well known in the art, such as distillation, fractionation, extraction and the like.

The major products of this syntheses are pyrazines, including, but not limited to 2,5-dimethyl-3-propylpyrazine, 2,5-dimethyl-3-ethylpyrazine, 2,3,5-trimethylpyrazine and 2,5-dimethylpyrazine. The principal by-products of these preparations are piperazines and their derivatives.

Yield, as defined herein, represents the efficiency in catalyzing the desired reaction relative to other undesired reactions. In this instance synthesis of pyrazines is the desired conversion. Yield is expressed as a molar percentile and is calculated by determining the molar amount of, for example, 2,5-dimethylpyrazine formed, divided by the molar amount of hydroxyamine charged and multiplying the quotient.

The products have been identified in this work by one or more of the following analytical procedures, viz, gas-liquid phase chromatography (glc), infrared (ir), mass spectrometry, proton nuclear magnetic resonance (H'-nmr) and elemental analyses, or a combination of these techniques. All temperatures are in degrees centrigrade and all pressures are in pounds per square inch gauge (psig).

Having described the inventive process, the following examples are submitted to supply specific and illustrative embodiments.

EXAMPLE 1

A 300-ml stirred autoclave with Pyrex liner was charged with a mixture of 1-amino-2-propanol (9.1 g, 0.12 mol), tributylphosphine (0.8 ml), ruthenium trichloride (0.265 g), and p-dioxane (20 ml). The reactor was sealed and purged of air. The reactor was heated to 180° C. and held for 5 hours. During this process, the pressure within the reactor reached 250 psi. The reaction mix was then allowed to cool to room temperature, and the gas formed during the reaction was vented. The product liquid (29.89) was recovered and analyzed.

A 52.8% yield of 2,5-dimethylpyrazine and 13.3% yield of 2,5-dimethylpiperazine were obtained, with 99% conversion of the 1-amino-2-propanol charged.

EXAMPLES 2–7

A variety of catalysts and conditions were tested for the cyclocondensation of 1-amino-2-propanol using the method of Example 1. The results are shown in Table I.

TABLE I

| Exp. | Catalyst | Ratio of Catalyst to Hydroxyamine w/w | Temp., °C. | Time, Hr | Max Press., psi | Conversion % | Yield, % 2,5-dimethyl-pyrazine | Yield, % 2,5-dimethyl-piperazine |
|---|---|---|---|---|---|---|---|---|
| 1. | RuCl$_3$—Bu$_3$P | 0.029 | 180 | 5 | 150 | 99.3 | 52.8 | 13.3 |
| 2. | RuCl$_3$—Bu$_3$P | 0.018 | 165 | 12 | 350 | 51.2 | 29.1 | 2.3 |
| 3. | RuCl$_2$(PPh$_3$)$_3$ | 0.01 | 180 | 12 | 200 | 16.3 | 10.9 | 0.9 |
| 4. | RuCl$_3$—Ph$_2$P—(CH$_2$)$_3$PPh$_2$ | 0.016 | 180 | 11 | 300 | 30.4 | 12.6 | 5.7 |
| 5. | RhCl$_3$—Ph$_2$P—(CH$_2$)$_3$PPh$_2$ | 6.25 × 10$^{-4}$ | 180 | 9 | 300 | 9.1 | 6.0 | 0.3 |
| 6. | PdCl$_2$(PPh$_3$)$_2$ | 0.01 | 180 | 10 | 100 | 6.1 | 2.9 | 0.5 |
| 7. | HRh(CO)(PPh$_3$)$_3$ | 0.005 | 180 | 12 | 350 | 65.9 | 23.3 | 10.3 |

EXAMPLE 8

The 1-amino-2-butanol (43 g, 0.48 mol), ruthenium trichloride (0.52 g) and tributylphosphine (1.6 ml) were subjected to a reaction as described in Example 1 above except that the solvent was tetraglyme (30 ml). A 23% yield of 2.5-diethylpyrazine and a 17% yield of 2,5-diethylpiperazine were obtained with 61% conversion of 1-amino-2-butanol.

What is claimed is:

1. A process for preparing pyrazines which comprises the steps of cyclocondensation of a hydroxyamine from the group consisting of ethanolamine, 1-amino-2-butanol, 1-amino-3-butanol and 1-amino-2-propanol in the presence of a catalyst consisting essentially of a rhodium, ruthenium or palladium-containing salt of hydrochloric acid and a phosphine containing compound from the group consisting of tri-n-butylphosphine, triphenylphosphine and 1,3-bis(diphenylphosphino)propane at a temperature of at least 100° C. and at atmospheric pressure to 400 psi.

2. The process of claim 1 wherein the hydroxyamine is from the group consisting of 1-amino-2-propanol and 1-amino-2-butanol.

3. The process of claim 1 wherein the rhodium salt of a mineral acid is rhodium(III) chloride.

4. The process of claim 1 wherein the ruthenium salt of a hydrochloric acid is ruthenium(III) chloride.

5. The process of claim 1 wherein the rhodium, ruthenium or palladium-containing compound and the phosphine-containing compound are added as a preformed complex.

6. The process of claim 5 wherein said complexes are selected from the group consisting essentially of tris(triphenylphosphine)ruthenium(II) chloride and bis(triphenylphosphine)palladium(II) chloride.

7. The process of claim 1 wherein the rhodium, ruthenium, or palladium-containing compound and the phosphine-containing compound are selected from the group consisting of the following combinations: $RuCl_3$—$Bu_3P$, $RuCl_3$—$Ph_2P(CH_2)_3PPh_2$ and $RhCl_3$—$Ph_2P(CH_2)_3PPh_2$.

8. The process of claim 1 wherein said cyclocondensation is conducted in the presence of an inert solvent.

9. The process of claim 8 is wherein said solvent is selected from the group consisting of cyclic, acyclic and heterocyclic ethers.

10. The process of claim 9 wherein the solvent is selected from the group consisting of p-dioxane and tetraglyme.

11. The process of claim 1 wherein the temperature is 150° C. to 250° C.

12. The process of claim 1 wherein the pressure is from 100 to about 400 psi.

* * * * *